United States Patent
Rubini et al.

(10) Patent No.: US 6,184,174 B1
(45) Date of Patent: Feb. 6, 2001

(54) CATALYSTS FOR DEHYDROGENATING ETHYLBENZENE TO STYRENE

(75) Inventors: Carlo Rubini, San Fermo Della Battaglia; Luigi Cavalli; Esterino Conca, both of Novara, all of (IT)

(73) Assignee: SUD Chemie MT S.R.L., Milan (IT)

( * ) Notice: Under 35 U.S.C. 154(b), the term of this patent shall be extended for 0 days.

(21) Appl. No.: 09/314,704

(22) Filed: May 19, 1999

(51) Int. Cl.[7] ............................. B01J 23/02; B01J 23/10; B01J 23/04; B01J 23/16
(52) U.S. Cl. ................ 502/304; 502/338; 502/330; 502/527.14; 502/527.16; 502/527.17
(58) Field of Search .......................... 502/304, 338, 502/527.14, 527.16, 330, 527.17

(56) References Cited

U.S. PATENT DOCUMENTS 4,698,325 * 10/1987 Andrew et al. ...................... 502/330
5,190,906    3/1993 Murakami et al. .

FOREIGN PATENT DOCUMENTS 0 297 685 A1   1/1989   (EP) .
WO 96/18458    6/1996   (WO) .

* cited by examiner

Primary Examiner—Elizabeth D. Wood
(74) Attorney, Agent, or Firm—Bryan Cave LLP

(57) ABSTRACT

Catalysts for dehydrogenating ethylbenzene to styrene which comprise iron oxide, oxides of alkaline and alkaline-earth metals, oxides of the lanthanide series, oxides of metals of the sixth group, prepared from a paste of iron oxide impregnated with an aqueous solution of a cerium salt, treated with aqueous KOH and calcined, after drying, to preform potassium ferrate, to which the other components or precursors of the catalyst are then added.

8 Claims, No Drawings

CATALYSTS FOR DEHYDROGENATING ETHYLBENZENE TO STYRENE

The present invention relates to catalysts for dehydrogenating ethylbeozone to styrene.

BACKGROUND OF THE INVENTION

The known type of catalysts for dehydrogenating ethylbenzene to styrene are based on iron oxide ($Fe_2O_3$) and comprise, as promoters and stabilizers, oxides of alkaline and alkaline-earth metals, oxides of elements of the lanthanide series, and oxides of metals of the sixth group of the periodic table.

The composition of the catalysts, expressed as a percentage of oxides by weight, comprises 50–92% iron oxide, 5–20% alkaline metal oxide, 0.5–14% alkaline-earth metal oxide, 2–10% oxide of elements of the lanthanide series and 0.5–6% oxide of metals of the sixth group.

Preferred compositions, expressed as oxides, comprise iron oxide, potassium oxide, calcium and/or magnesium oxides, cerium oxide and molybdenum and/or tungsten oxides.

In the catalysts, the iron oxide is partly present in the form of potassium ferrate.

Potassium ferrate is considered to be the active catalytic component.

SUMMARY OF THE INVENTION

It has now been found unexpectedly that it is possible to obtain catalysts which have high activity and selectivity in the reaction for the dehydrogenation of ethylbenzene to styrene even when operating with low, weight ratios (S/O) between the water used in the reaction and ethylbenzene.

DETAILED DESCRIPTION OF THE INVENTION

The catalysts of the invention comprise iron oxide ($Fe_2O_3$), oxides of alkaline and alkaline-earth metals, oxides of the lanthanide series, oxides of metals of the sixth group of the periodic table and potassium ferrate in the form of crystallites with numeral average size of less than 2 microns. The potassium ferrate of the catalysts is preformed by action of aqueous KOH on a paste of iron oxide impregnated with an aqueous solution of a cerium salt and by subjecting the paste, after drying, to calcination at temperatures from 600 to 900° C.

The other components or precursors of the catalyst are then added to the calcined product and blended and remixed with it.

The dried mixture is ground and then extruded so as to obtain granules of the catalyst in the intended shape. The granules are then subjected to calcination at 600–900° C. for 1–6 hours. It is surprising that the resulting catalysts have higher activities at low S/O ratios than the corresponding catalysts prepared by adding and mixing the components in a single step.

The possible use of low using S/O ratios allots considerable energy savings due to the smaller amount of steam used. It is also surprising that the catalysts according to the invention have high activities even at low S/O ratios, i.e., under conditions in which the dilution of the ethylbenzene is higher and its partial pressure in the system is therefore lower.

The composition of the catalysts according to the invention, expressed relation to the total weight of the catalyst, comprises: 50–90% iron oxide ($Fe_2O_3$), 5–15% potassium oxide, 2–15% calcium and/or magnesium oxide, 2–10% cerium oxide ($CeO_2$), 1–10% molybdenum and/or tungsten oxide.

Preferred compositions comprise:
a) 70–80% iron oxide, 8–10% potassium oxide, 8–10% cerium oxide, 2–5% calcium and magnesium oxide, 2–5% $MoO_3$, or
b) 70–80% iron oxide, 5–8% potassium oxide, 4–10% cerium oxide, 1–3% magnesium and/or calcium oxide, 4–7% $WO_3$.

Iron oxide ($Fe_2O_3$) is partly present as potassium ferrate $K_2O \cdot nFe_2O_3$, a being preferably 11, with numeral average size of the crystallites of less than 2 microns, particularly comprised within the range from 0.5 to 1.5 microns.

The size of the crystallites is determined by scanning electronic microscopy (SEM).

As mentioned, the catalysts according to the invention are prepared by first extruding a paste of hydrated iron oxide FeO(OH) (yellow hydrated iron oxide) with an aqueous solution of a soluble cerium salt, such as for example cerium nitrate) to which an aqueous solution of potassium hydroxide is added. The paste, after drying at 100–200° C., is calcined at 600–900° C. for 1–6 hours. The calcined product is ground, and then mixed with molybdenum trioxide and/or $WO_3$, magnesium and/or calcium carbonate and the paste, after drying at 100–200° C., is extruded to obtain the intended geometric shape and then calcined at 600–900° C. for 1–6 hours.

It is possible to use various geometric shapes, such as a solid cylinder, a hollow cylinder, or a cylinder with lobes and through holes which are parallel to the hole of the cylindrical granule and are substantially mutually equidistant.

The ratio between the surface and the volume of the granules in the case of catalysts in the form of three-lobed perforated granules is at least 2.4 $cm^{-1}$.

In these granules, the ratio between the height and the distance between the axes of the holes is in the range from 1.5 to 2.5.

Granule diameter is generally 3–4 mm and height is generally 3–5 mm.

Cylindrical granules of this kind are described in EP-A-591792, which description is herewith incorporated by reference.

The perforated and lobate granules are prepared by pressure molding, using the external lubrication technique: in other words, the lubricant is disposed on the surface of the mold chamber and of the male plug used to form the holes instead of being included in the mass of the powder to be tableted.

Solid lubricants, such as magnesium stearate and stearic acid, are preferably used.

The use of catalysts in the form of lobated and perforated granules make it possible one to significantly reduce pressure drops in fixed-bed reactors and to improve catalytic activity and selectivity.

The reaction for dehydrogenating ethylbenzene to styrene is carried out according to known methods, by passing a stream of ethylbenzene and water vapor through a fixed bed of the catalyst, working at temperatures from 540° C. to 650° C., with pressures which are equal to, or higher or lower than, the atmospheric pressure and with a water/ethylbenzene weight ratio from 2.4 to 1.5 and preferably lower than 2. The space velocity of the ethylbenzene stream is 0.5 $cm^3/cm^3$ fixed bed/h.

The following examples are given by way of non-limitative illustration of the invention.

EXAMPLE 1

A paste was prepared by mixing yellow hydrated iron oxide first with an aqueous solution of cerium nitrate, then with an aqueous solution of KOH. The paste was dried at 150° C. for 2 hours and then calcined at 850° C. for 2 hours.

The calcined product was ground and then mixed with an aqueous suspension of molybdenum trioxide, magnesium and calcium carbonate, extruded and then dried at 150° C. for 2 hours. The dried mixture was ground and tabletted so as to form three-lobed cylindrical granules with through holes at the lobes, said holes being parallel to each other and to the axis of the cylinder.

The inside diameter of the holes was 1.3 mm the wall thickness was 0.8 mm, the diameter of the circumference of the granules was 2.5 nm and the height was 5 mm. The holes were located at the vertices of an equilateral triangle. Tabletting was carried out by using stearic acid as an external lubricant, applied with a continuous stream of air on the wall of the mold chamber and on the male plug for the through holes.

The granules were calcined at 650 ° C. for 4 hours.

The components were used in such amounts as to obtain the following final composition, in relation to the weight of the catalyst: $Fe_2O_3$=77%, $K_2O$=9.6%, $CeO_2$=7%, MgO=2% CaO=2% $MoO_3$=2.4%.

The axial ultimate tensile stress (in the direction of the axis of the cylinder) was 25N/particle.

Pore volume was 0.2 cm$^3$/g and consisted of 25% pores with a radius from 800 to 1000 A, 50% pores with a radius from 1000 to 2000 A, and 10% pores with a radius from 2000 to 4000 A.

Pores with a radius of more than 50,000 A were not present.

The catalyst surface area was 4 m$^2$/g. Bulk density was 0.97 g/cm$^3$.

The numeral average size of the crystallites was 1 micron (determined by scanning electronic microscopy (SEM)).

COMPARISON EXAMPLE 1

A paste was prepared by mixing hydrated yellow iron oxide with cerium nitrate, KOH, $MoO_3$, $MgCO_3$, and $CaCO_3$ and water.

The extruded mixture was dried at 150° C. for 2 hours and ground and then tabletted as in Example 1 and calcined at 850° C. for 2 hours.

The final composition was as in Example 1: the surface area was 5.3 m$^2$/g, pore volume was 0.28 cm$^3$/g and bulk density was 0.87 g/cm$^3$.

EXAMPLE 2

The catalysts of Example 1 and of Comparison Example 1 were tested in a steel reactor with an inside diameter of 35 mm.

During each test, 200 cm$^3$ of catalyst were placed in the reactor and supported by a steel grille.

The tests were conducted at 590° C., varying the weight ratio between water vapor and ethylbenzene (S/O), which reagents were made to flow through the catalytic bed after being preheated to 590° C.

The pressure at the outlet of the reactor was 1.05 ate and the hourly space velocity of the ethylbenzene was 0.5 cm$^3$/cm$^3$ fixed bed/h. Samples of the reaction products were collected over 2 hours after the system had been stabilized for at least 20 hours for each condition.

Conversion and Solar selectivity are listed in the following table.

TABLE 1

|  | S/O | Conv. % | Select. % |
|---|---|---|---|
| Example 1 | 2.4 | 66.8 | 94.8 |
|  | 2 | 62.4 | 95.0 |
| Comparison | 2.4 | 66.2 | 94.7 |
| Example 1 | 2 | 56.9 | 95.1 |

What is claimed is:

1. Catalysts for dehydrogenating ethylbenzene to styrene, comprising iron oxide ($Fe_2O_3$), potassium oxide, magnesium and/or calcium oxides, cerium oxide, tungsten and/or molybdenum oxides and potassium ferrate wherein the numeral average size of the crystallites of said potassium ferrate is less than 2 microns and said potassium ferrate is preformed prior to the addition of the magnesium and/or calcium oxides or the precursors thereof, and tungsten and/or molybdenum oxides or the precursors thereof, by action of aqueous KOH on a paste of hydrated iron oxide impregnated with the aqueous solution of a cerium salt and drying and calcinating the resultant paste.

2. Catalysts according to claim 1, wherein calcination of the dried paste is carried out from 600 to 900° C.

3. Catalysts according to claim 1, wherein the potassium ferrate has a numeral average size of the crystallites from 0.5 to 1.5 microns.

4. Catalysts according to claim 1, wherein the catalysts have the following composition, expressed as a percentage of oxides in relation to the total weight of the catalyst: 50–90% iron oxide, 5–15% potassium oxide, 2–15% calcium and/or magnesium oxide, 2–10% cerium oxide ($CeO_2$), 1–10% molybdenum oxide ($MoO_3$) and/or tungsten oxide ($WO_3$).

5. Catalysts according to claim 4, wherein the composition of the catalyst, expressed as a percentage of oxides in relation to the total weight of the catalyst comprises: 70–80% iron oxide, 8–10% potassium oxide, 8–10% cerium oxide, 2–5% calcium and/or magnesium oxides, 2–5% $MoO_3$.

6. Catalysts according to claim 4, wherein the composition, expressed as a percentage of oxides in relation to the total weight of the catalyst is: 70–80% iron oxide, 5–8% potassium oxide, 4–10% cerium oxide ($CeO_2$), 1–3% magnesium and/or calcium oxide, 4–7% tungsten oxide ($WO_3$).

7. Catalysts according to claim 1 in the form of cylindrical granules with lobes and through holes at the lobes.

8. Catalysts according to claim 7, wherein the granules have three lobes and through holes at the lobes, with axes which are substantially parallel to those of the cylinder and are mutually equidistant.

* * * * *